United States Patent [19]

Gruber et al.

[11] 4,212,938

[45] Jul. 15, 1980

[54] REAGENT AND METHOD FOR THE DETERMINATION OF CHOLESTEROL

[75] Inventors: Wolfgang Gruber, Garatshausen; Hans U. Bergmeyer, Tutzing; Erich Bernt, Munich; Alexander Hagen, Tutzing; Peter Roeschlau, Tutzing; Gunter Lang, Tutzing; Klaus Beaucamp, Tutzing, all of Fed. Rep. of Germany

[73] Assignee: Boehringer Mannheim GmbH, Mannheim-Waldhof, Fed. Rep. of Germany

[21] Appl. No.: 360,515

[22] Filed: May 15, 1973

[30] Foreign Application Priority Data

May 17, 1972 [DE] Fed. Rep. of Germany ....... 2224132

[51] Int. Cl.² .............................................. C12Q 1/50
[52] U.S. Cl. ...................................... 435/11; 435/19; 435/291
[58] Field of Search ..................... 195/103.5 R; 435/11

[56] References Cited

U.S. PATENT DOCUMENTS

| | | | |
|---|---|---|---|
| 3,099,605 | 7/1963 | Free .............................. | 195/103.5 R |
| 3,282,803 | 11/1966 | Poepel et al. ................. | 195/103.5 R |
| 3,607,093 | 9/1971 | Stone ............................. | 195/103.5 R |
| 3,776,816 | 12/1973 | Terada et al. ................. | 195/103.5 R |

FOREIGN PATENT DOCUMENTS

2047147 12/1971 France .............................. 195/103.5 R

OTHER PUBLICATIONS

Schatz et al., J. Bact., vol. 58, pp. 117-125 (1949).
Colowick et al., Methods in Enzymology, vol. I, pp. 678-681 (1955).
Heftmann et al., Biochemistry of Steroids, pp. 14-16 (1960).

*Primary Examiner*—Alvin E. Tanenholtz
*Attorney, Agent, or Firm*—Sprung, Felfe, Horn, Lynch & Kramer

[57] ABSTRACT

Cholesterol is determined by incubating a sample suspected of containing cholesterol in an aqueous medium with cholesterol oxidase and determining either the oxygen consumption, the hydrogen peroxide formed, or cholestenone, as a measure of the initial cholesterol content; reagent compositions comprising cholesterol oxidase and a system for the determination of $H_2O_2$ or for the determination of cholestenone are provided.

20 Claims, 4 Drawing Figures

REAGENT AND METHOD FOR THE DETERMINATION OF CHOLESTEROL

This invention relates to a method for the enzymatic determination of free and esterified cholesterol and a reagent for carrying out this method.

The determination of cholesterol is of considerable importance in medical diagnosis. An increased cholesterol level in the blood constitutes an important risk factor of arteriosclerosis. In the presence of high cholesterol values, i.e., hypercholesterolemia, coronary insufficiency and myocardial infarctions occur more frequently than in the presence of low cholesterol values. Hypercholesterolemia favors the occurence of arteriosclerosis and coronary diseases and, therefore, needs to be recognized early in order for treatment to begin in time. Increased cholesterol values are likewise frequently present in the case of diabetes mellitus, nephrotic syndrome, hypothyreosis and liver diseases such as biliary cirrhosis. A quick and reliable method for the determination of cholesterol is, therefore, of great importance.

The known and usable methods for the determination of cholesterol are based on the reaction according to Liebermann and Buchard. According thereto, both free and esterified cholesterol form with acetic acid anhydride and concentrated sulfuric acid blue-green colored compounds, the color intensity of which is proportional to the cholesterol concentration and is measured spectrophotometrically.

However, this known method exhibits important disadvantages. The main disadvantage of this method consists in its non-specificity. The Liebermann-Burchard reaction constitutes a relatively non-specific steroid reaction in which other steroids participate in addition to cholesterol. Since, for instance, there are present in the plasma also 1 to 3% dihydrocholesterol and 0.5% to 1.4% $\Delta^7$-cholestenol in addition to other steroids, an undesirably large error results. Moreover, this reaction is interfered with by bilirubin and hemoglobin, which results in increased and, thus, incorrectly positive cholesterol values. A further disadvantage consists in that aggressive and corrosive reagents have to be used.

Therefore, there has been a need for a method and an agent for the determination of cholesterol, which do not have the aforementioned disadvantages and, particularly, for an absolutely specific method for cholesterol which does not require aggressive reagents.

In accordance with the invention, this object is achieved. Essentially, the method of the invention for the determination of cholesterol comprises incubating cholesterol in an aqueous medium with cholesterol oxidase and determining either the oxygen consumption or formed $H_2O_2$ or cholestenone, as a measure of initial cholesterol content.

Cholesterol oxidase is a new enzyme which catalyzes the reaction below:

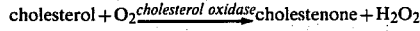
cholesterol + $O_2$ $\xrightarrow{cholesterol\ oxidase}$ cholestenone + $H_2O_2$ The above reaction takes place quantitatively and, thus permits an absolutely specific and accurate quantitative determination of cholesterol.

Cholesterol oxidase, the starting material for its preparation, its purification and its properties are described in U.S. Ser. No. 360,490 now U.S. Pat. No. 4,144,129.

The method according to the invention is suitable for the determination of cholesterol in aqueous media of all types such as food extracts, body fluids, and particularly serum. Because of the great specificity of the method, only free cholesterol is determined. However, it is also possible to determine bound cholesterol, which as is known, is present in esterified form, by prior chemical or enzymatic saponification. Chemical saponification is done, for instance, with alcoholic caustic potash solution, enzymatic saponification is done with esterase, preferably with cholesterol esterase from the liver or pancreas.

The oxygen consumption, $H_2O_2$ formation or cholestenone formation in accordance with the above general equation can be measured by the known and customary methods.

Suitable methods for the determination of the oxygen consumption are, for instance, gas chromatography and depolarization method. The polarometric determination by means of oxygen electrode is preferred, since this method is particularly suitable for the determination of cholesterol by automatic control mechanisms. Appropriate methods of determination are known. The methods for the polarometric measurement of the oxygen consumption in aqueous media, which have proven particularly suitable, are described in U.S. Pat. No. 3,838,011.

The hydrogen peroxide formed can be determined both titrimetrically and potentiometrically, polarographically and colorimetrically and well as enzymatically. The enzymatic methods using catalase or peroxidase are preferred, since they are not only extremely specific and reliable, but can also be combined in a very simple manner with the main reaction with formation of hydrogen peroxide. The method that has been found especially suitable is the determination by means of catalase in the presence of $\beta$-diketones such as, for instance, acetyl acetone and a lower aliphatic mono- or polyvalent alcohol such as methanol, ethanol or methylene glycol, as well as the determination by means of peroxidase in the presence of a chromogen. In the determination by means of catalase, acetyl acetone and methanol, the latter is oxidized to formaldehyde, which, together with acetyl acetone, enters into a color reaction which can be measured. In the determination by means of peroxidase, compounds are added as chromophore, which can be determined photometrically following the reaction. An example for a suitable chromophore is 2,2'-aminobenzothiazoline sulfonic acid.

Cholestenone is determined by means of keto-reagents, preferably a hydrazine derivative reacting with keto-groups under formation of hydrazone such as, for instance, 2,4-dinitrophenyl hydrazine. However, cholestenone can also be determined directly by measuring the absorption at 240 nm.

A further object of the invention is a reagent for the determination of cholesterol, consisting of cholesterol oxidase and a system for the determination of $H_2O_2$ or a system for the determination of cholestenone. In a first preferred embodiment, this reagent consists of cholesterol oxidase, catalase, acetyl acetone, methanol, and buffers containing ammonium ions, separately or in a mixture. In a further preferred embodiment, this reagent consists of cholesterol oxidase, peroxidase, chromogen and buffer, separately or in mixture. 2,2'-aminobenzthiazoline sulfonic acid is preferred as chromogen.

In accordance with a further preferred embodiment, the reagent of the invention consists of cholesterol oxidase and a hydrazine derivative reacting with ketogroups with formation of hydrazone as well as, in a given case, a buffer, 2,4- dinitrophenyl hydrazine is preferred as hydrazine derivative.

In addition to the aforementioned necessary constituents, the aforementioned preferred reagent combinations preferably also contain customary solvents, stabilizers and surface-active substances. All of these additives are known to the person skilled in the art and customary in systems for the determination of hydrogen peroxide and cholestenone resp.

It is preferable that the aforementioned reagent combinations contain the essential constituents in the following quantitative ratios:

1. 13-150 U of cholesterol oxidase as well as $2 \times 10^4$ to $5 \times 10^5$ of commercially available catalase, 0.05 to 0.2 ml. of acetyl acetone and 2 to 10 ml. of methanol in 100 ml. of ammonium ion—containing buffer, pH 5 to 7, as well as 0.02 to 0.3 ml. of a surface-active agent (preferably hydroxypolyethoxydodecane).

2. 3 to 40 U of cholesterol oxidase as well as $2 \times 10^2$ to $1 \times 10^4$ U of commercially available peroxidase, 50 to 200 mg. of 2,2'-aminobenzthiazoline sulfonic acid as well as 0.05 to 0.5 ml. of surface-active agent (preferably hydropolyethoxydodecane) in 100 ml. of buffer, pH 6 to 8.

3. 0.1 to 1 U of cholesterol oxidase, 1 to 5 ml. of a 1 mM solution of 2,4-dinitrophenyl hydrazine and, if desired, 0.005 to 0.1 ml. of surface-active agent.

4. 2 to 100 U of cholesterol oxidase as well as 0.1 to 2.0 ml. of surface-active agent (preferably hydroxypolyethoxydodecane) in 50 ml. of buffer, pH 5 to 9, preferably 0.5 M sodium phosphate buffer, pH 7.5.

The following examples illustrate the invention further as do the drawings hereof in which.

EXAMPLE 1—Polarometric determination of the oxygen consumption

Figure 1:
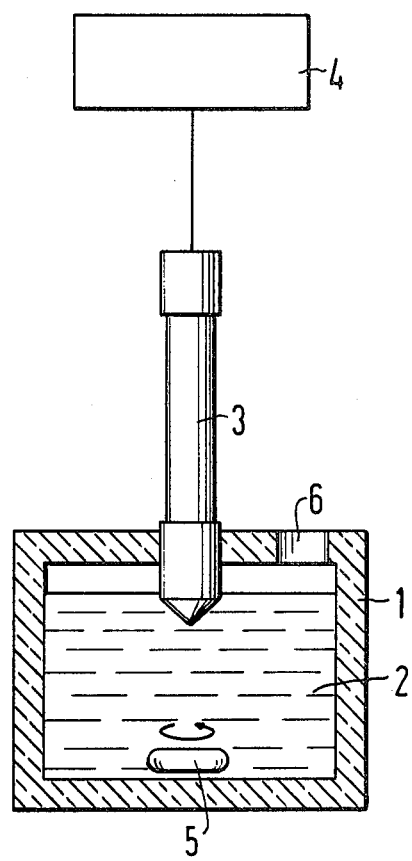
FIG. 1 is a schematic representation of apparatus usable in the invention.
Figure 2:
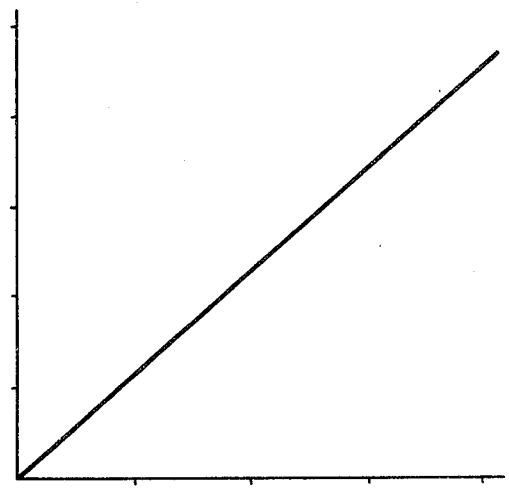
FIG. 2 is a plot of oxygen consumption v. cholesterol concentration.

The apparatus shown in FIG. 1 of the attached drawing was utilized. The apparatus consisted of a reaction vessel 1 in the form of a cylindrical chamber of transparent plastic having an inside diameter of 143 mm. and an inside height of 220 mm. The chamber contained 1.8 ml. of a solution of 18 mM of potassium iodide, 7.5 mM of ammonium heptamolybdate, 800 mM of sodium chloride and 2 U of cholesterol oxidase in 0.2 m of potassium phosphate buffer pH 6.0. The detector 3 consisted of an oxygen-sensitive electrode (WTW:OXI electrode E 016) protruded into the reaction vessel. The detector was connected with the analyzer 4 (WTW: digital meter DIGI 610 with feed-in OXI 610 D). A magnetic stirrer 5 is disposed at the bottom of the reaction vessel 1. 20 ul of an aqueous cholesterol-containing solution were added as sample through the feed opening 6. While stirring vigorously with the magnetic stirrer, the drop in the oxygen concentration of the solution was measured. The oxygen consumption measured after a reaction time of 2.5 minutes was plotted against the cholesterol concentration. The result of measurement for different concentrations of the cholesterol-containing solution was shown in FIG. 2 of the attached drawing. It showed the linear dependency between measured signal and cholesterol concentration.

The process was repeated using a serum sample saponified by means of alcoholic KOH. The determination yielded a concentration of 193 mg. of cholesterol/100 ml. A comparison value according to Liebermann and Burchard yielded 182 mg./100 ml.

EXAMPLE 2—Determination of $H_2O_2$ 10 g. of ammonium hydrogen phosphate were dissolved in 100 ml. of water and adjusted to pH 7.0 using 85% phosphoric acid. Thereupon, $10^5$ U of catalase were added. A mixture of 0.2 ml. of acetyl acetone and 10 ml. of methanol was brought up to 100 ml. using the solution obtained in the manner described above.

Figure 3:
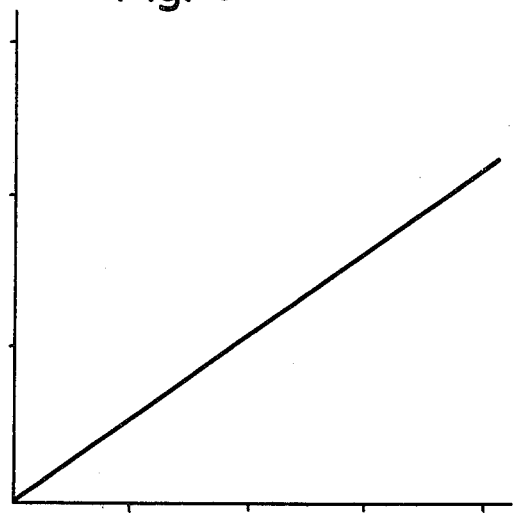
FIGS. 3 and 4 are calibration curves.

7.5 ml. of the solution obtained in this manner were mixed with 0.5 ml. of serum and 0.5 ml. of a cholesterol standard solution containing 200 mg.% of cholesterol resp. Aliquots of the serum-containing sample as well as of the sample containing the cholesterol standard solution were each mixed with 5 U of cholesterol oxidase and 0.02 ml. of a 10% hydroxypolyethoxydodecane solution and incubated at 37° C. for 70 minutes. Thereupon, the dye formed at 405 nm was measured photometrically taking into account the blank value of the reagent. A calibration curve was prepared using the cholesterol standard solutions, which was shown in FIG. 3 of the drawing. In the calibration curve the cholesterol concentration was plotted against the extinction at 405 nm.

The cholesterol content of the serum-containing sample was determined using a standard as reference value. Control determinations according to Liebermann-Burchard yielded a deviation of approximately 5%.

EXAMPLE 3—Determination of $H_2O_2$ 0.05 ml. of a 20% solution of hydroxypolyethoxydodecane and 0.02 ml. (=36 U) of commercially available peroxidase solution as well as 0.02 ml. of $H_2O_2$ (0.02 ml. of 30% v:v $H_2O_2$ per 100 ml. of water) for removing reducing substances were added to 3 ml. of potassium phosphate buffer pH 7 ($O_2$ saturated) containing 100 mg% of 2,2'-aminobenzthiazoline sulfonic acid. The mixture was observed in the photometer at 405 nm and 436 nm resp. As soon as the reaction has stopped, 0.01 ml. of serum (diluted with water 1:15) were used for starting. After 10 minutes 0.15 U of cholesterol oxidase were added. After another 10 minutes the extinction difference was read off.

Figure 4:
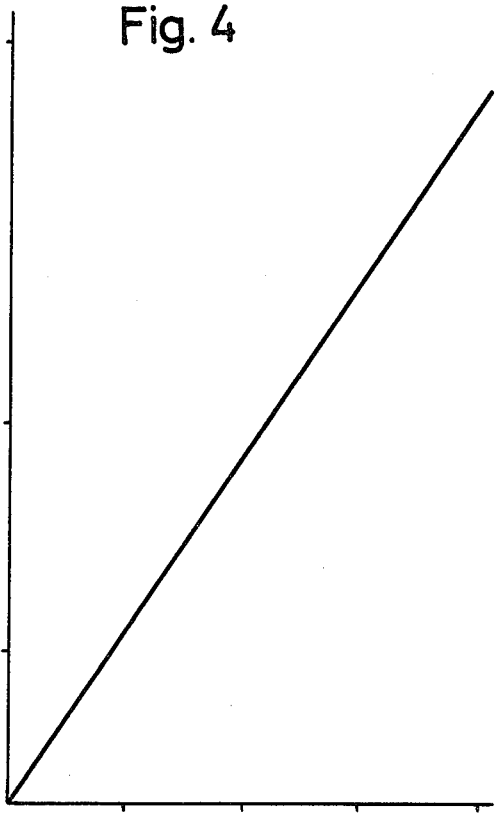

In the same manner, but using a cholesterol standard solution containing 200 mg.%, the calibration curve shown in FIG. 4 was prepared. The cholesterol content of the serum sample was determined by means of this calibration curve. The measurement yielded a content of 180 mg.% of cholesterol. A control measurement according to Liebermann and Burchard yielded 185 mg.%.

EXAMPLE 4—Determination of Cholestenone 0.2 ml. of serum (diluted with water 1:10) were mixed with 0.05 ml. of 20% hydroxypolyethoxydodecane solution and 0.15 U of cholesterol oxidase. After 15 minutes 2.0 ml. of a solution were added, which contained 1 mM of 2,4-dinitrophenyl hydrazine in 1 N hydrochloric acid. After another 30 minutes 4.0 ml. of water were added, and the hydrazone formed was measured at 405 nm in the photometer. The evaluation was done using a standard curve, taking into account the blank value of the reagent. The measurement can also be carried out at 546 nm after adding alkali.

The measurement of a typical sample yielded 60 mg.% of free cholesterol and 154 mg.% of total cholesterol (saponification with alcoholic KOH).

The comparative determination according to Liebermann-Buchard yielded 170 mgs. of total cholesterol.

For the saponification of esterified cholesterol (measurement of total cholesterol in the serum), 1 ml. of serum, 1 ml. of 20% hydroxypolyethoxydodecane solution and 5 ml. of 0.5 N KOH in 90% ethanol were mixed and heated to 70° C. for 30 minutes. Thereupon the solution was left to cool, mixed with 10 ml. of 0.1 M magnesium sulfate solution and centrifuged off. The supernatant (13 ml.) contained the total cholesterol in free form.

The saponification of esterified cholesterol using liver esterase was done by incubating the serum at 37% C. and pH 6 to 8 for 30 minutes.

EXAMPLE 5

0.2 ml. of serum were added to 2.5 ml. of 0.5 M sodium phosphate buffer, pH 7.5, with 0.4% hydroxypolyethoxydodecane. The extinction ($E_1$) was read off at 240 nm in a suitable spectrum photometer, and the reaction was started with 0.02 ml. (=1.5 U) of cholesterol oxidase. After 2 minutes, the extinction ($E_2$) was again read off. The concentration of the cholestenone formed and, thus, of the cholesterol resulted from the difference between the first and second reading, taking into account the molar extinction coefficient for cholestenone at 240 nm.

The measurement of a typical sample yielded 58 mg.% of free cholesterol and 163 mg.% of total cholesterol (after saponification).

The comparative determination according to Burchard yielded 173 mg.% of total cholesterol.

It will be understood that the specification and examples are illustrative but not limitative of the present invention and that other embodiments within the spirit and scope of the invention will suggest themselves to those skilled in the art.

What is claimed is:

1. A test composition for determining total cholesterol in a biological fluid sample comprising a chemical system having cholesterol ester hydrolase activity, a chemical system having cholesterol oxidase activity, and means for determining at least one of the reaction products produced when free cholesterol is contacted with said chemical system having cholesterol oxidase activity.

2. Method for the determination of cholesterol in a sample comprising incubating the sample in an aqueous medium with cholesterol esterase and cholesterol oxidase, characterized by its ability to convert cholesterol to cholestenone with the formation of hydrogen peroxide, and determining either the oxygen consumption, the $H_2O_2$ formed, or cholestenone as a measure of the initial cholesterol content in the sample.

3. Method as claimed in claim 2 wherein the $H_2O_2$ formed is determined and the determination is made enzymatically using catalase or peroxidase.

4. Method as claimed in claim 2 wherein the cholestenone formed is measured, directly at 240 nm or using a ketoreagent such as 2,4-dinitrophenyl hydrazine.

5. Method as claimed in claim 2 wherein oxygen consumption is determined polarometrically as a measure of the cholesterol initially present.

6. Test composition as claimed in claim 1 comprising a system for the determination of cholestenone.

7. Test composition as claimed in claim 1 comprising a system for the determination of $H_2O_2$.

8. Test composition as claimed in claim 1 comprising a a system for the determination of oxygen consumption.

9. Test composition as claimed in claim 1 comprising cholesterol oxidase, cholesterol esterase and a system for the determination of $H_2O_2$.

10. Test composition as claimed in claim 7 wherein said system for the determination of $H_2O_2$ comprises a catalase, a $\beta$-diketone, a lower aliphatic alcohol and a buffer.

11. Test composition as claimed in claim 10 wherein the $\beta$-diketone is acetyl acetone and the lower aliphatic alcohol is methanol.

12. Test composition as claimed in claim 7 wherein the system for the determination of $H_2O_2$ comprises peroxidase, a chromogen and a buffer.

13. Test composition as claimed in claim 8 wherein the system for the determination of cholestenone comprises a derivative reacting with keto-groups.

14. Test composition as claimed in claim 13 wherein said derivative is 2,4-dinitrophenyl hydrazine.

15. Test composition as claimed in claim 6 comprising:
    13 to 150 U of cholesterol oxidase
    $2 \times 10^4$ to $5 \times 10^5$ U of catalase
    0.5 to 0.2 ml. of acetyl acetone
    2 to 10 ml. of methanol in 100 ml. of ammonium ion-containing buffer, pH 5 to 7
    0.05 to 0.5 ml of surface—active agent.

16. Test composition as claimed in claim 12 comprising:
    3 to 40 U of cholesterol oxidase
    $2 \times 10^2$ to $1 \times 10^4$ U of commercially available peroxidase
    50 to 200 mg. of 2,2'-aminobenzthiazoline sulfonic acid
    0.05 to 0.5 ml. of surface-active agent in 100 ml. of buffer, pH 6 to 8.

17. Test composition as claimed in claim 13 comprising:
    0.1 to 1 U of cholesterol oxidase
    1 to 5 ml. of a 1 mM solution of 2,4-dinitrophenyl hydrazine and
    0.005-0.1 ml. of a surface agent.

18. Test composition as claimed in claim 1 additionally containing a surface active agent.

19. Method as claimed in claim 2 wherein said sample is a body fluid.

20. Method for the determination of cholesterol in a biological fluid sample which comprises contacting said sample with a chemical system having cholesterol ester hydrolase activity, a chemical system having cholesterol oxidase activity, and means for determining at least one of the reactants or one of the reaction products produced as a measure of the initial cholesterol content.

* * * * *